United States Patent [19]
Stinson

[11] Patent Number: 5,980,564
[45] Date of Patent: Nov. 9, 1999

[54] BIOABSORBABLE IMPLANTABLE ENDOPROSTHESIS WITH RESERVOIR

[75] Inventor: Jonathan S. Stinson, Plymouth, Minn.

[73] Assignee: Schneider (USA) Inc., Plymouth, Minn.

[21] Appl. No.: 08/905,806

[22] Filed: Aug. 1, 1997

[51] Int. Cl.[6] .............................. A61F 2/06; A61F 2/02; A61F 2/04; A61M 29/00
[52] U.S. Cl. .................................. 623/1; 623/11; 623/12; 606/191; 606/194
[58] Field of Search .............................. 623/1, 2, 11, 12, 623/66; 606/191, 192, 194

[56] References Cited

U.S. PATENT DOCUMENTS

| | | | |
|---|---|---|---|
| 4,202,349 | 5/1980 | Jones | 128/689 |
| 4,447,239 | 5/1984 | Krütten | 604/282 |

(List continued on next page.)

FOREIGN PATENT DOCUMENTS

| | | | |
|---|---|---|---|
| 0183372A1 | 6/1986 | European Pat. Off. | |
| 0679372A2 | 11/1995 | European Pat. Off. | |
| 0709068A2 | 5/1996 | European Pat. Off. | |
| 0689807A3 | 8/1996 | European Pat. Off. | |
| 0775472A2 | 5/1997 | European Pat. Off. | |
| 8002641 | 12/1980 | WIPO . | |
| 9001969 | 3/1990 | WIPO . | |
| 9004982 | 5/1990 | WIPO . | |
| 9110766 | 7/1991 | WIPO . | |
| 9216166 | 10/1992 | WIPO . | |
| 9406372 | 3/1994 | WIPO . | |
| 9406373 | 3/1994 | WIPO . | |
| 9605872 | 2/1996 | WIPO . | |
| 9640000 | 12/1996 | WIPO . | |
| WO 97/11724 | 4/1997 | WIPO | A61L 27/00 |
| WO 98/18408 | 5/1998 | WIPO | A61F 2/06 |

OTHER PUBLICATIONS

Advertisement for Spire Corporation radiopaque coating technology, Medical Products Manufacturing News, Mar. 1977, p. 30.

Studies on a new radiopaguepolymeric biomaterial, A. Benzina, M.A.B. Kruft, F. Bar, F.H. van deer Veen, C.W. Bastiaansen, V. Heijnen, C. Reutelingsperger, and L.H. Koole, Biomaterials 1994, vol. 15 No. 14, pp. 1122–1128.

Deformation Characteristics of a Bioabsorbable Intravascular Stent, C. Mauli Agrawal, Ph.D., PE. and Howard G. Clark, Ph.D., Investigative Radiology, Dec. 1992, vol. 27, pp. 1020–1024.

Studies on radio–opaque polymeric biomaterials with potential applications to endovascular protheses, M. Kruft, A. Benzina, R. Blezer, and L. Koole, Biomaterials 1996, vol. 17, No. 18, pp. 1803–1812.

Advertisement for radiopaque polymers for medical device maunfacturing, New England Urethane, Inc.

Gianturco–Roubin Flex–Stent GRII, M–D–D–I Report—"The Gray Sheet", Mar. 4, 1996.

Seventh Complex Coronary Angioplasty Course, May 1996, p. 257.

Synthetic Bioabsorbable Polymers, Thomas H. Barrows, Ph.D., High Performance Biomaterials, Szycher ed., pp. 243–257.

Wound Closure Biomaterials and Devices, C.C. Chu, J.A. von Fraunhofer, amd H.P. Greisler, CTC Press, Boca Raton, FL, 1997 pp. 131–235.

In Vitro Degradation of Polylactides Depending on Different Processes, M. Dauner, E. Muller, B. Wagner, and H. Planck, Degradation Phenomena on Polymeric Biomaterials, H. Planck, M. Dauner, M. Renardy (eds), Springer–Verlag, Berlin, 1992, pp. 107–122.

(List continued on next page.)

*Primary Examiner*—Mickey Yu
*Assistant Examiner*—Dinh X. Nguyen
*Attorney, Agent, or Firm*—Larkin, Hoffman, Daly & Lindgren, Ltd.

[57] ABSTRACT

A bioabsorbable implantable endoprosthesis having elongate elements including hollow, cavity or porous portions adapted to accumulate by-product from the degradation of the bioabsorbable material and shortening the diffusion distance for water absorption and thereby relatively increasing the degradation of the structure.

22 Claims, 7 Drawing Sheets

U.S. PATENT DOCUMENTS

| | | | |
|---|---|---|---|
| 4,475,972 | 10/1984 | Wong | 156/167 |
| 4,681,110 | 7/1987 | Wiktor | 128/343 |
| 4,693,234 | 9/1987 | Hoffman et al. | 128/1 |
| 4,722,344 | 2/1988 | Cambron et al. | 128/658 |
| 4,738,740 | 4/1988 | Pinchuk et al. | 156/167 |
| 4,787,391 | 11/1988 | Elefteriades | 128/654 |
| 4,968,317 | 11/1990 | Törmäläet al. | 606/77 |
| 5,015,183 | 5/1991 | Fenick | 433/76 |
| 5,024,232 | 6/1991 | Smid et al. | 128/654 |
| 5,026,377 | 6/1991 | Burton et al. | 606/108 |
| 5,047,050 | 9/1991 | Arpesani | 623/1 |
| 5,059,211 | 10/1991 | Stack et al. | 606/198 |
| 5,061,275 | 10/1991 | Wallstén et al. | 623/1 |
| 5,085,629 | 2/1992 | Goldberg et al. | 604/8 |
| 5,116,360 | 5/1992 | Pinchuk et al. | 623/1 |
| 5,133,660 | 7/1992 | Fenick | 433/76 |
| 5,133,742 | 7/1992 | Pinchuk | 623/1 |
| 5,160,341 | 11/1992 | Brenneman et al. | 606/198 |
| 5,163,951 | 11/1992 | Pinchuk et al. | 623/1 |
| 5,177,170 | 1/1993 | Sarpeshkar et al. | 528/76 |
| 5,201,757 | 4/1993 | Heyn et al. | 606/198 |
| 5,203,777 | 4/1993 | Lee | 604/280 |
| 5,229,431 | 7/1993 | Pinchuk | 521/159 |
| 5,256,158 | 10/1993 | Tolkoff et al. | 604/280 |
| 5,306,286 | 4/1994 | Stack et al. | 606/198 |
| 5,320,602 | 6/1994 | Karpiel | 604/54 |
| 5,346,981 | 9/1994 | Sarpeshkar et al. | 528/85 |
| 5,354,257 | 10/1994 | Roubin et al. | 600/7 |
| 5,366,504 | 11/1994 | Andersen et al. | 623/11 |
| 5,405,402 | 4/1995 | Dye et al. | 623/22 |
| 5,415,546 | 5/1995 | Cox, Sr. | 433/213 |
| 5,419,760 | 5/1995 | Narciso | 604/8 |
| 5,423,849 | 6/1995 | Engelson et al. | 606/191 |
| 5,429,617 | 7/1995 | Hammersmark et al. | 604/264 |
| 5,433,727 | 7/1995 | Sideris | 606/213 |
| 5,441,517 | 8/1995 | Kensey et al. | 606/213 |
| 5,464,450 | 11/1995 | Buscemi et al. | 623/6 |
| 5,464,650 | 11/1995 | Berg et al. | 427/2.3 |
| 5,478,352 | 12/1995 | Fowler | 606/213 |
| 5,484,444 | 1/1996 | Braunschweiler et al. | 606/108 |
| 5,498,227 | 3/1996 | Mawad | 600/3 |
| 5,500,013 | 3/1996 | Buscemi et al. | 623/1 |
| 5,527,337 | 6/1996 | Stack et al. | 606/198 |
| 5,527,354 | 6/1996 | Fontaine et al. | 623/1 |
| 5,545,208 | 8/1996 | Wolff et al. | 623/1 |
| 5,551,954 | 9/1996 | Buscemi et al. | 523/1 |
| 5,556,413 | 9/1996 | Lam | 606/198 |
| 5,591,172 | 1/1997 | Bachmann et al. | 606/108 |
| 5,591,222 | 1/1997 | Susawa et al. | 623/1 |
| 5,591,224 | 1/1997 | Schwartz et al. | 623/1 |
| 5,591,226 | 1/1997 | Trerotola etal. | 623/1 |
| 5,609,627 | 3/1997 | Goicoechea et al. | 623/1 |
| 5,624,411 | 4/1997 | Tuch | 604/265 |
| 5,628,755 | 5/1997 | Heller et al. | 606/108 |
| 5,628,787 | 5/1997 | Mayer | 623/1 |
| 5,628,788 | 5/1997 | Pinchuk | 623/1 |
| 5,630,840 | 5/1997 | Mayer | 623/1 |
| 5,645,559 | 7/1997 | Hachtman et al. | 606/198 |
| 5,653,747 | 8/1997 | Dereume | 623/1 |
| 5,662,703 | 9/1997 | Yurek et al. | 623/1 |
| 5,670,161 | 9/1997 | Healy et al. | 424/426 |
| 5,674,277 | 10/1997 | Freitag | 623/1 |
| 5,674,286 | 10/1997 | D'Alessio et al. | 623/11 |
| 5,676,146 | 10/1997 | Scarborough | 128/654 |
| 5,683,448 | 11/1997 | Marcade | 623/1 |
| 5,697,969 | 12/1997 | Schmitt et al. | 623/1 |
| 5,700,285 | 12/1997 | Myers et al. | 623/1 |
| 5,725,517 | 3/1998 | DeBusk | 604/362 |
| 5,725,567 | 3/1998 | Wolff et al. | 623/1 |
| 5,725,572 | 3/1998 | Lam et al. | 623/1 |
| 5,741,327 | 4/1998 | Frantzen | 623/1 |
| 5,762,625 | 6/1998 | Igaki | 604/8 |
| 5,843,158 | 12/1998 | Lenker, et al. | 623/1 |
| B1 4,655,771 | 9/1996 | Wallsten | 623/1 |
| B1 4,954,126 | 5/1996 | Wallstén | 600/36 |

OTHER PUBLICATIONS

Long–term in vivo degradation and bone reaction to various polylactides, P. Mainil–Varlet, B. Rahn, and S. Goglewski, Biomaterials 1997, vol. 18, No. 3, pp. 257–266.

Current Status of Biodegradable Stents, J.F., Tanguay, M.D., J.P. Zidar, M.D., H.R. Phillips, III, M.D., and R. S. Stack, M.D., Cardiology Clinics, vol. 12, No. 4, Nov. 1994, pp. 699–713.

Perspectives on the In Vivo Responses of Biodegradable Polymers, James M. Anderson, M.D., Ph.D., CTC Press Inc., (1995) pp. 223–233, 1995.

Advances in Controlled Release Technology: Polymeric Delivery System for Drugs, Pesticides and Foods: New Methods of Drug Delivery, Robert Langer, Science vol. 249, pp. 1527–1533.

Advances in Controled Release Technology: Polymeric Delivery System s for Drugs, Pesticides and Foods: Fundamentals pf pH. and Temperature–Sensitive Polymers, Nicholas A. Peppas, pp. 32–45.

*Bioabsorbable Stent and Method of Making the Same*, Assignee: Duke University.

Enhancement of the Mechanical Properties of Polylactides by solid–state extrusion, Walter Weiler and Sylwester Gogolewski, Biomaterials 17 (1996), pp. 529–535.

*The Physics of Radiology*, H.E. Johns and J. R. Cunningham, pp. 137–142.

Bicomponent vascular grafts consisting of synthetic absorbable fibers. I. In Vitro Study, Tarng–Jenn Yu and C.C. Chu, Journal of Biomedical Materoa;s Research, vol. 27, 1329–1339 (1993).

Biomedical Applications of Synthetic Biodegradable Polymers, Editited by Jeffrey O. Hollinger, D.D.S., Ph.D., CTC Press, p. 21.

Development of a Polymer Endovascular Prothesis and Its Implantation in Porcine Arteries, William J. Van der Giessen, M.D., et al., Journal of Interventional Cardiology, vol. 5, No. 3, 1992, pp. 175–185.

Role of Polymers in improving the results of stenting in coronary arteries, Tao Peng, et al., Biomaterials 1996, vol. 17, No. 7, pp. 685–694.

Bioabsorbable, Drug–Eluting, Intracoronary Stents: Design and Future Applications, R.S. Schwartz, et al., Coronary Stents (1992), pp. 135–154.

Ten Years of Stenting: What Next?, Ulrich Sigwart, M.D., FRCP, FACC, FESC, Journal of Interventional Cardiology, vol. 10, No. 3, pp. 195–205.

Biocompatibility of solid poly (ortho ester), M. Ekholm, et al., Journal of Materials Science: Materials in Medicine 8, (1997), pp. 265–269.

The Polymer Stent, Jean–François Tanguay, et al., Endoluminal Stenting, pp. 216–225.

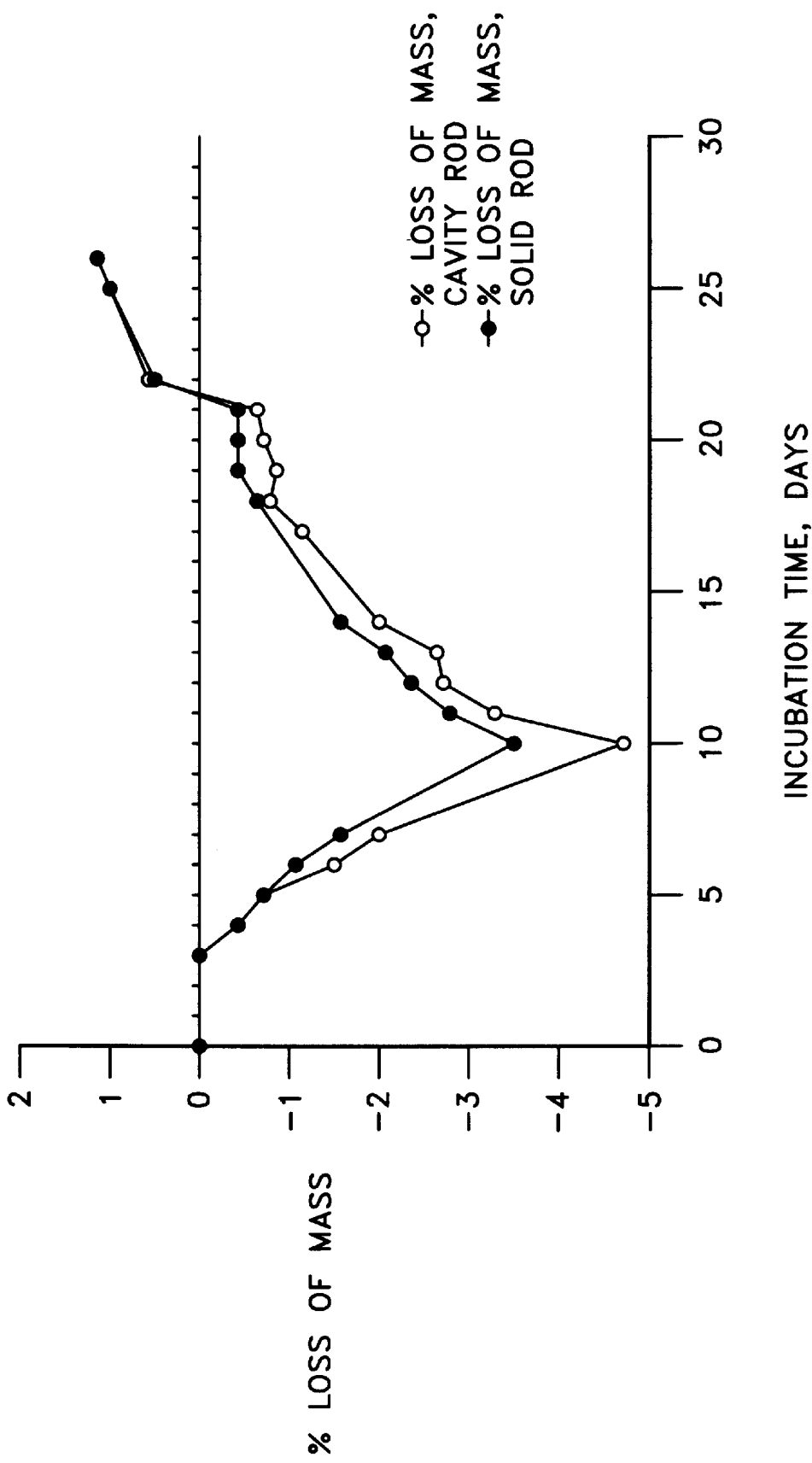

BIOABSORBABLE IMPLANTABLE ENDOPROSTHESIS WITH RESERVOIR

BACKGROUND OF THE INVENTION

This invention relates generally to a bioabsorbable implantable endoprosthesis having one or more reservoir portions including hollow, cavity, or porous portions to accumulate by-products of degradation.

Self-expanding medical prostheses frequently referred to as stents are well known and commercially available. They are, for example, disclosed generally in the Wallsten U.S. Pat. No. 4,655,771, the Wallsten et al. U.S. Pat. No. 5,061,275 and in Hachtmann et al., U.S. Pat. No. 5,645,559. Devices are used within body vessels of humans for a variety of medical applications. Examples include intravascular stents for treating stenoses, stents for maintaining openings in the urinary, biliary, tracheobronchial, esophageal, and renal tracts, and vena cava filters.

A delivery device which retains the stent in its compressed state is used to deliver the stent to a treatment site through vessels in the body. The flexible nature and reduced radius of the compressed stent enables it to be delivered through relatively small and curved vessels. In percutaneous transluminal angioplasty, an implantable endoprosthesis is introduced through a small percutaneous puncture site, airway, or port and is passed through various body vessels to the treatment site. After the stent is positioned at the treatment site, the delivery device is actuated to release the stent, thereby allowing the stent to self-expand within the body vessel. The delivery device is then detached from the stent and removed from the patient. The stent remains in the vessel at the treatment site as an implant.

Stents must exhibit a relatively high degree of biocompatibility since they are implanted in the body. An endoprosthesis may be delivered into a body lumen on or within a surgical delivery system such as preferred delivery devices shown in U.S. Pat. Nos. 4,954,126 and 5,026,377. Suitable materials for use in such delivery devices are described in U.S. patent application Ser. No. 08/833,639, filed Apr. 8, 1997. The stents of the present invention may be delivered by alternative methods or by using alternative devices.

Commonly used materials for known stent filaments include Elgiloy® and Phynox® metal spring alloys. Other metallic materials than can be used for self-expanding stent filaments are 316 stainless steel, MP35N alloy, and superelastic Nitinol nickel-titanium. Another self-expanding stent, available from Schneider (USA) Inc. of Minneapolis, Minn., has a radiopaque clad composite structure such as shown in U.S. Pat. No. 5,630,840 to Mayer. Self-expanding stents can be made of a Titanium Alloy as described in U.S. patent application Ser. No. 08/598,751, filed Feb. 8, 1996.

The strength and modulus of elasticity of the filaments forming the stents are also important characteristics. Elgiloy®, Phynox®, MP35N and stainless steel are all high strength and high modulus metals. Nitinol has relatively lower strength and modulus.

The implantation of an intraluminal stent will preferably cause a generally reduced amount of acute and chronic trauma to the luminal wall while performing its function. A stent that applies a gentle radial force against the wall and that is compliant and flexible with lumen movements is preferred for use in diseased, weakened, or brittle lumens. The stent will preferably be capable of withstanding radially occlusive pressure from tumors, plaque, and luminal recoil and remodeling.

There remains a continuing need for self-expanding stents with particular characteristics for use in various medical indications. Stents are needed for implantation in an ever growing list of vessels in the body. Different physiological environments are encountered and it is recognized that there is no universally acceptable set of stent characteristics. The strength and modulus of elasticity of the filaments forming the stents are important characteristics.

A need exists for a stent which has self expanding characteristics, but which is bioabsorbable. A surgical implant such as a stent endoprosthesis must be made of a non-toxic, biocompatible material in order to minimize the foreign-body response of the host tissue. The implant must also have sufficient structural strength, biostability, size, and durability to withstand the conditions and confinement in a body lumen.

All documents cited herein, including the foregoing, are incorporated herein by reference in their entireties for all purposes.

SUMMARY OF THE INVENTION

The present invention is an improved implantable medical device comprised of a tubular, radially compressible, axially flexible and radially self-expandable structure including elongate filaments having reservoir portion. The filaments are formed in a braid-like configuration. The filaments consist of a bioabsorbable polymer which exhibits a relatively high degree of biocompatibility.

Briefly, self-expanding stents of the present invention are formed from a number of resilient filaments which are helically wound and interwoven in a braided configuration. The stents assume a substantially tubular form in their unloaded or expanded state when they are not subjected to external forces. When subjected to inwardly directed radial forces the stents are forced into a reduced-radius and extended-length loaded or compressed state. The stents are generally characterized by a longitudinal shortening upon radial expansion.

In one preferred embodiment, the device is a stent which substantially consists of a plurality of elongate polylactide bioabsorbable polymer filaments, helically wound and interwoven in a braided configuration to form a tube.

There is a need for a bioabsorbable implantable endoprosthesis that has a high rate of degradation and may be tailored to degrade over predetermined periods of time. One way to avoid long-term complications from an implant is to make the implant bioabsorbable so that the device is naturally eliminated from the treatment site after it has served its intended function.

Such a bioabsorbable implantable endoprosthesis would be especially advantageous for medical procedures requiring an endoprosthesis for short term or temporary use. For example, it would be advantageous to implant an implantable endoprosthesis that functions for a specific period of time and does not require a surgical procedure for removal at the end of its functional lifetime. With such an endoprosthesis, there is no need to remove the endoprosthesis because the bioabsorbable material therein decomposes over a period of time into non-toxic biological substances (e.g. lactic acid and glycolic acid) which are easily metabolized or excreted by the body. Such a bioabsorbable implantable endoprosthesis would be advantageous in urological, biliary, vascular, and airway applications where use is desired for only weeks, months, or a few years while a benign stricture is cured or healed, or for use in pre-operative palliation. Such a device may also offer an advantage in that shorter resorption times may reduce the time of inflammatory response and may reduce scarring.

Bioabsorbable implantable endoprostheses of the present invention include stents, stent-grafts, grafts, filters, occlusive devices, and valves which may be made of poly(alpha-hydroxy acid) such as polylactide [poly-L-lactide (PLLA), poly-D-lactide (PDLA)], polyglycolide (PGA), polydioxanone, polycaprolactone, polygluconate, polylactic acid-polyethylene oxide copolymers, poly (hydroxybutyrate), polyanhydride, polyphosphoester, poly (amino acids), or related copolymers materials, each of which have a characteristic degradation rate in the body. For example, PGA and polydioxanone are relatively fast-bioabsorbing materials (weeks to months) and PLA and polycaprolactone are relatively slow-bioabsorbing material (months to years).

An implantable endoprosthesis constructed of a bioabsorbable polymer provides certain advantages relative to metal stents such as natural decomposition into non-toxic chemical species over a period of time. Also, bioabsorbable polymeric stents may be manufactured at relatively low manufacturing costs since vacuum heat treatment and chemical cleaning commonly used in metal stent manufacturing are not required.

An implantable endoprosthesis made of substantially solid elongate members consisting of PLA generally will require 1–3 years to absorb in a body. However, an implantable endoprosthesis made of PLA, having comparatively shorter resorption times than 1–3 years is desirable for certain indications such as pediatric endoluminal interventions where anatomical growth rates are high and implant size revisions are often necessary. The endoprosthesis of the present invention would be advantageous because the endoprosthesis would absorb over a relatively shorter time and removal thereof would be unnecessary. As the child grows, the appropriate size implantable endoprosthesis could be placed in the body when needed. The resorption time for an implantable endoprosthesis made of a poly (alpha-hydroxy acid) polymer having elongate members including hollow, cavity, or porous portions may be reduced to several days or a few weeks for PGA or to several months to years for PLA.

The period of time that a bioabsorbable implantable endoprosthesis is functional is dependent upon the degradation rate of the bioabsorbable material and the environment into which it is implanted. The degradation rate of a bioabsorbable endoprosthesis is dependent on chemical composition, processing methods, dimensions, sterilization methods, and geometry of the reservoir portions (i.e. hollow, cavity, or porous portions) of the present invention.

Bioabsorbable polymer stents are radiolucent and the mechanical properties of the polymers are generally lower than structural metal alloys. Bioabsorbable stents may require radiopaque markers and may have a larger profile on a delivery catheter and in a body lumen to compensate for the lower material properties.

Bioabsorbable PLLA and PGA material are degraded in vivo through hydrolytic chain scission to lactic acid and glycolic acid, respectively, which in turn is converted to $CO_2$ and then eliminated from the body by respiration. Heterogeneous degradation of semicrystalline polymers occurs due to the fact that such materials have amorphous and crystalline regions. Degradation occurs more rapidly at amorphous regions than at crystalline regions. This results in the product decreasing in strength faster than it decreases in mass. Totally amorphous, cross-linked polyesters show a more linear decrease in strength with mass over time as compared to a material with crystalline and amorphous regions. Degradation time may be affected by variations in chemical composition and polymer chain structures, and material processing.

PLA monofilaments may be produced by a process involving seven general steps as summarized herein. First, a polymer formed of poly-L-lactic acid is brought to an elevated temperature above the melting point, preferably 210°–230° C. Second, the material is then extruded at the elevated temperature into a continuous fiber, by a conventional process, at a rate of from about three to four feet per minute. Third, the continuous fiber is then cooled to cause nucleation. The cooling is preferably performed by passing the fiber through a nucleation bath of water. Fourth, the material then passes through a first puller, which runs at about the same speed as the extruder, and places the material under slight tension. Fifth, the fiber is then heated to a temperature between about 60° C. and about 90° C. (preferably 70° C.) as it passes through a heated oven. To perform annealing, the oven can be designed to be quite long and heated near the end, so that the orientation and annealing take place in the same oven. Alternatively, a separate oven can be placed directly after the orientation oven. The annealing step heats the fibers to a range of about 65° C. to about 90° C., preferably closer to 90° C. Sixth, while being heated in the orientation oven and the annealing oven, the fiber is drawn between the first puller located before the orientation oven and a second puller located after the annealing oven (if a separate oven). The material is drawn at a draw ratio of between about 5 to about 9, preferably between about 6 and about 8. Draw ratio describes either the reduction in diameter or the extension in length resulting from polymer extrusion or drawing. Quantitatively, the drawing ratio is a unitless value equal to the extruded or drawn length divided by the original length. Maintaining tension through the annealing step prevents shrinkage in later use. The second puller, located at the exit of the oven, runs at an increased speed necessary to provide the desired draw ratio. As the fiber exits the oven and passes through the second puller the tension is immediately released before the material cools. Seventh, finally, the fiber is collected onto spools of desired lengths.

Strength of the filaments generally increases with draw ratio and with lower draw temperatures. A draw ratio of between 5 and 9 is preferred. PLA is generally amorphous because of the material's slow crystallization kinetics. Very slow cooling after drawing of the filament or use of a nucleating agent will cause crystallization. However, the material may be annealed at temperatures above about 60° C. to cause crystallization, and generally, the strength decreases slightly and the modulus increases. Annealing is preferably performed after drawing to release residual stresses and to homogenize the surface to center variations in structure. Annealing will preferably be performed at a temperature of between about 60° C. and 150° C. for a period of time between about 5 and 120 minutes.

An endoprosthesis with hollow filaments and closed filament ends can be made by braiding individual strands of extruded tubing. The polymer is melt-extruded through a die containing a center mandrel such that the product is a hollow tube strand. The tube strands are collected onto spools and in a separate operation are transferred from the spools to braid bobbins. After braiding the tubular strands the braid is transferred from the braid mandrel to an anneal mandrel and annealed at a temperature between the glass transistion temperature and the melt temperature of the polymer. The annealed stents are slid off of the anneal mandrel and are cut to the desired endoprosthesis length by clipping each strand in the stent with wire cutters. As the cutting surfaces of the wire cutters close upon the strand the polymer is crimped or flowed and the hollow center is thereby closed. The tubular strands are closed at each end of the stent as a result of the strand cutting operation and the hollow portions are thus generally sealed to prevent significant drainage of accumulating polymer degradation products. It is not necessary for the ends of the hollow strands in a stent to always be sealed closed since capillary forces that would draw the degradation products toward any open ends or that would draw in bodily fluids would not act over such long lengths as with a helical interbraided strand in a stent.

Reference is made to Enhancement of the Mechanical properties of polylactides by solid-state extrusion, W. Weiler and S. Gogolewski, Biomaterials 1996, Vol. 17 No. 5, pp. 529–535; and Deformation Characterstics of a Bioabsorbable Intravascular Stent, Investigative Radiology, December 1992, C. Mauli, Agrawal, Ph.D., P.E., H. G. Clark, Ph.D., pp. 1020–1024.

Mechanical properties generally increase with increasing molecular weight. For instance, the strength and modulus of PLA generally increase with increasing molecular weight. Degradation time generally decreases with decreasing initial molecular weight (i.e., a stent made of a low molecular weight polymer would be bioabsorbed before a stent made of a high molecular weight polymer). Low molecular weight PLA is generally more susceptible to thermo-oxidative degradation than high molecular weight grades, so an optimum molecular weight range should be selected to balance properties, degradation time, and stability. The molecular weight and mechanical properties of the material generally decrease as degradation progresses. PLA generally has a degradation time greater than 1 year. Ethylene oxide sterilization process (EtO) is a preferred method of sterilization. PLA has a glass transition temperature of about 60° C., so care must be taken not, to store products in environments where high temperature exposure greater than 60° C. may result in dimensional distortion.

PLA, PLLA, PDLA and PGA include tensile strengths of from about 40 thousands of pounds per square inch (ksi) to about 120 ksi; a tensile strength of 80 ksi is typical; and a preferred tensile strength of from about 60 ksi to about 120 ksi. Polydioxanone, polycaprolactone, and polygluconate include tensile strengths of from about 15 ksi to about 60 ksi; a tensile strength of about 35 ksi is typical; and a preferred tensile strength of from about 25 ksi to about 45 ksi.

PLA, PLLA, PDLA and PGA include tensile modulus of from about 400,000 pounds per square inch (psi) to about 2,000,000 psi; a tensile modulus of 900,000 psi is typical; and a preferred tensile modulus of from about 700,000 psi to about 1,200,000 psi. Polydioxanone, polycaprolactone, and polygluconate include tensile modulus of from about 200,000 psi to about 700,000 psi; a tensile modulus of 450,000 psi is typical; and a preferred tensile modulus of from about 350,000 psi to about 550,000 psi.

PLLA filament has a much lower tensile strength and tensile modulus than, for example, Elgiloy® metal alloy wire which may be used to make braided stents. The tensile strength of PLLA is about 22% of the tensile strength of Elgiloy®. The tensile modulus of PLLA is about 3% of the tensile modulus of Elgiloy®. Stent mechanical properties and self-expansion are directly proportional to tensile modulus of the material. As a result, a PLLA filament braided stent made to the same design as the metal stent has low mechanical properties and would not be functional. The polymeric braided stents should have radial strength similar to metal stents and should have the required mechanical properties capable of bracing open endoluminal strictures.

The term "substantially degrades" means that the stent has lost at least 50% of its structural strength. It is preferable that the stent lose about 100% of its structural strength. The included angle between interbraided filaments in the axial orientation is termed "braid angle" prior to annealing and is termed "filament crossing angle" after annealing. A braid becomes a stent after annealing.

Bioabsorbable resins such as PLLA, PDLA, PGA and other bioabsorbable polymers are commercially available from several sources including PURAC America, Inc. of Lincolnshire, Ill.

In sum, the invention relates to a bioabsorbable implantable endoprosthesis comprising a tubular, radially compressible, axially flexible, and radially self-expandable braided and annealed structure having a diameter in a free state, the structure including from about 10 to about 36 filaments including poly (alpha-hydroxy acid), the structure having a radial force of from about 40 grams to about 300 grams at about one-half diameter, each filament having a tensile strength of from about 20 ksi to about 120 ksi, and a tensile modulus of from about 400,000 psi to about 2,000,000 psi, and an average diameter of from about 0.15 mm to about 0.6 mm, the filaments having a crossing angle of from about 120 degrees to about 150 degrees in a free state, each filament including one or more reservoir portions with an average cross-sectional area greater than about $7.9 \times 10^{-7}$ mm$^2$ and in each filament, the sum of the one or more reservoir portions when empty represents a total volume percentage greater than about 5% of the total filament volume. The bioabsorbable implantable endoprosthesis of claim 1 wherein the sum of the one or more reservoir portions when empty represents a total volume percentage of from about 20% to about 40%. The degradation by-products may at least partially collect in the reservoir portions. The degradation by-products in the reservoir portions may have an average pH level which decreases over time in vivo. The reservoir portions may be hollow, cavity, porous, or combinations thereof. The average pH level in the reservoir may be between about 3 and 7. The endoprosthesis may substantially degrades in vivo in less than 3 years. The endoprosthesis may provides structural integrity to a body lumen for less than 2 years. The filaments may be monofilament, multi-filament, ribbon, suture, thread, fiber, or combinations thereof. The implantable endoprosthesis may be a stent, stent-graft, graft, filter, occlusive device, or valve. The filaments may gain weight in vivo in an amount of from about 0.1% to about 20% of initial mass prior to losing weight in an amount of from about 0.1% to about 70% of initial mass prior to disintegration. The reservoir portions may accumulate the degradation by-product for a predetermined amount of time. The filaments may comprise PLLA, PDLA, or combinations thereof and substantially degrade in vivo in from about 1 year to about 2 years. The filaments may comprise polylactide, polyglycolide, or combinations thereof and substantially degrade in vivo in from about 3 months to about 1 year. The filaments may comprise polyglycolide, polygluconate, polydioxanone, or combinations thereof and substantially degrade in vivo in from about 1 week to about 3 months. The thickness of the filament t, in mm, may be equal to about (D/(1.8D+15)) ±0.03 mm, where D, in mm, is the free state diameter. The number of filaments, N, may be equal to about (D/(0.022D+0.17)) ±4 filaments, where D, in mm, is the free state diameter. The endoprosthesis may have at least one end of diminishing diameter. The filaments may have a tensile modulus of from about 700,000 to about 1,200,000 psi. The endoprosthesis may have a braid angle of from about 60 degrees to about 150 degrees when implanted in vivo. The filament may further comprises a water absorption diffusion distance of from about 1 micron to about 250 microns.

The invention also relates to a bioabsorbable implantable endoprosthesis comprising one or more elongate elements including poly (alpha-hydroxy acid), each filament including one or more reservoir portions with an average cross-sectional area greater than about $7.9 \times 10^{-7}$ mm$^2$, and in each filament, the sum of the one or more reservoir portion when empty represents a total volume % greater than about 10% wherein the poly (alpha-hydroxy acid) bioabsorbs and degradation by-products therefrom collect in the reservoir. The hollow portions when empty may represent a volume percentage of at least 5 percent, cavity portions when empty may represent a volume percentage of at least 5 percent, and porous portions when empty may represent a volume percentage of at least 10 percent.

The invention also relates to a method of using an implantable endoprosthesis including: disposing a implantable endoprosthesis made of poly (alpha-hydroxy acid) in a delivery system, the endoprosthesis comprising a tubular, and radially expandable structure made of elongate filaments including hollow, cavity, or porous portions. Each portion with an average cross-sectional area greater than about $7.9 \times 10^{-7}$ mm$^2$ and the sum of the portions when empty represent a total volume % greater than about 10%; inserting the delivery system and endoprosthesis in a body lumen; deploying the endoprosthesis from the delivery system into the body lumen; and allowing the hollow, cavity, or porous portions to accumulate degradation by-product from the poly (alpha-hydroxy acid).

The invention also relates to a method of manufacturing an implantable endoprosthesis comprising the steps: disposing a braided bioabsorbable polymer endoprosthesis on an annealing mandrel, the endoprosthesis comprising a tubular, and radially expandable structure made of elongate elements. The elongate elements including at least one hollow, cavity, or porous portion. Each portion with an average cross-sectional area greater than about $7.9 \times 10^{-7}$ mm$^2$ and the sum of the portions when empty have a total volume % greater than about 10%; axially compressing the endoprosthesis; annealing the endoprosthesis at a temperature less than the melting point of the endoprosthesis for a time of from about 5 minutes to about 90 minutes; and cooling the endoprosthesis. The annealing temperature may be from about 130° C. to about 160° C. and the annealing time is from about 10 minutes to about 20 minutes. The method may further comprise the step of cutting the endoprosthesis into predetermined lengths. The method may further comprise a step of braiding the endoprosthesis on a braiding mandrel at a braid angle of from about 90 degrees to about 150 degrees. The method while annealing, the endoprosthesis has a braid angle of from about 130 degrees to about 150 degrees.

The invention also relates to a bioabsorbable endoprosthesis including at least one elongate element having an outer surface and a thickness. The element consisting of a bioabsorbable polymer which readily degrades in vivo. The element including one or more pores in diameter of from about 1 micron to about 20 microns. The pores when empty represent a volume percentage of from about 10% to about 50%. The pores accumulate by-product from the degradation of the bioabsorbable material.

The invention also relates to a bioabsorbable implantable endoprosthesis consisting essentially of a poly (alpha-hydroxy acid). The endoprosthesis prior to implantation having an outer surface containing a multitude of empty pores which open on the endoprosthesis outer surface and which have an average depth of at least about 0.5 micron. A sum of the pores have a total pore outer surface area at their outer openings on the outer surface of the endoprosthesis. The endoprosthesis has a total outer surface area which includes the total pore outer surface area, and the total pore outer surface area is from about 2 to about 40 percent of the total endoprosthesis surface area. The pores when empty may have an average cross-sectional area on the filament outer surface of at least about $7.9 \times 10^{-7}$ mm$^2$. The pores when empty may have an average cross-sectional area on the filament outer surface of less than about $3.1 \times 10^{-4}$ mm$^2$. The pores when empty may have an average cross-sectional area on the filament outer surface of from about $7.9 \times 10^{-5}$ to about $1.8 \times 10^{-4}$ mm$^2$.

The invention also relates to a bioabsorbable implantable endoprosthesis including at least one elongate element consisting essentially of poly (alpha-hydroxy acid). The element has an outer surface. The elongate element prior to implantation containing at least one empty internal cavity which does not open to the element outer surface. The at least one cavity has an average cross-sectional area along a length of the element. The element has an average cross-sectional area along its length which includes the average cavity cross-sectional area, and the average cavity cross sectional area is from about 2 to about 40 percent of the average element cross-sectional area. The cavity when empty may have an average cross-sectional area of from about 10 to about 30 percent of the elongate element cross-sectional area.

The invention also relates to bioabsorbable implantable stent having a tubular, radially compressible and self-expandable braided and annealed structure including a first set of filaments each of which extends in a helix configuration along a center line of the stent and having a first common direction of winding; and a second set of filaments each of which extends in a helix configuration along a center line of the stent and having a second common direction of winding. The second set of filaments crossing the first set of filaments at an axially directed angle so as to form a plurality of interstices between filaments. A plurality of filaments have a length including PLLA, PDLA, PGA, or combinations thereof and having prior to implantation an empty lumen extending at least substantially through the entire length of the plurality of filaments. The plurality of filaments have further a tensile strength of from about 20 ksi to about 120 ksi, a tensile modulus of from about 400,000 psi to about 2,000,000 psi, and an average diameter of from about 0.15 mm to about 0.6 mm. The first set of filaments and second set of filaments act upon one another to create an outwardly directed radial force sufficient to implant the stent in a body vessel upon deployment from a delivery device. The second set of filaments may cross the first set of filaments at an axially directed angle of between about 120 and about 150 degrees when the stent is in a first free radially expanded state after being annealed but before being loaded on a delivery device. The stent may have a second free radially expanded state after being loaded and then released from a deployment device. The first and second sets of filaments may cross at an axially directed angle of between about 80 and 145 degrees when in the second free radially expanded state. The first and second sets of filaments may cross at an axially directed angle of between about 90 and 100 degrees when in the second free radially expanded state and the stent may have an outside diameter of between 3 and 6 mm when in the second free radially expanded state. The axially directed angle may be between about 110 and 120 when in the second free radially expanded state. The stent may have an outside diameter when in the second free radially expanded state and the stent may exert an outwardly directed radial force at one half of the outside diameter of from about 40 grams to about 300 grams. The stent may have an implanted state after being loaded, subsequently released from a deployment device, deployed into a body vessel, and then implanted in the body vessel, with the first and second sets of filaments crossing at an axially directed angle of between about 95 and 105 degrees when the stent is in the implanted state.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

BRIEF DESCRIPTION OF THE DRAWINGS

FIG. 6 is a graph showing a comparison of the loss of mass over time for a PLLA solid rod and a PLLA cavity rod.

DETAILED DESCRIPTION OF THE INVENTION

Figure 1:
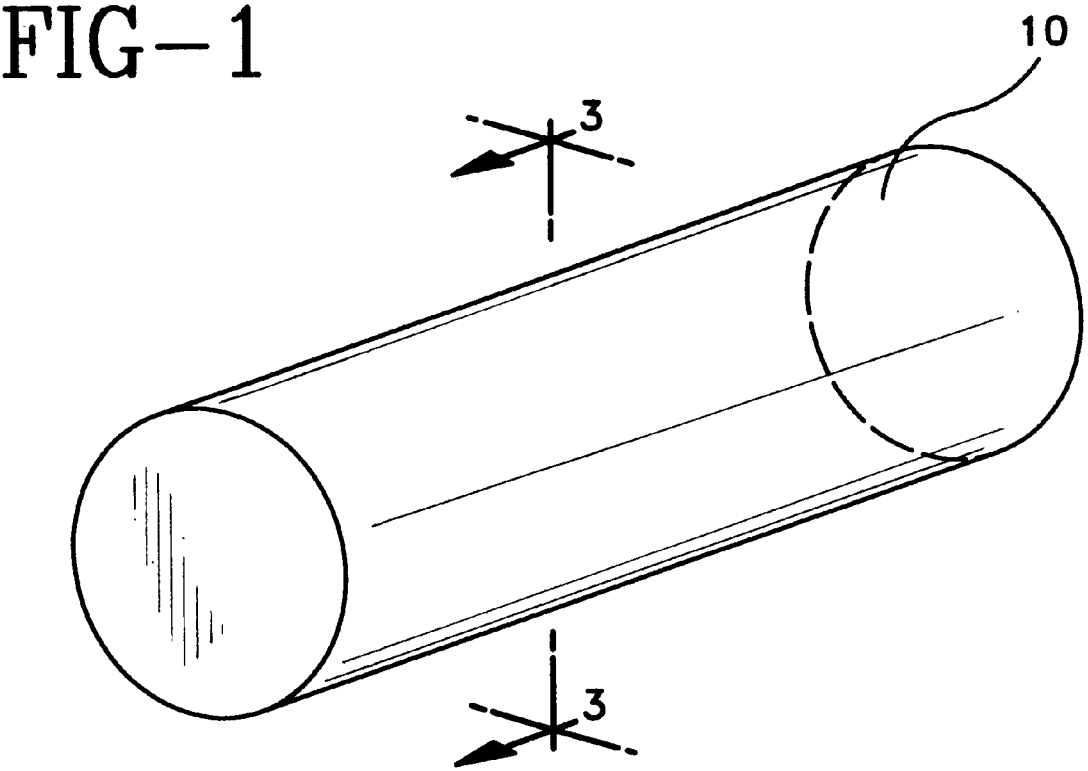
FIG. 1 is a side view of a elongate element.

Reference is made to the example shown in FIG. 1 illustrating a substantially solid elongate member 10 made of a bioabsorbable material such as PLLA or PGA.

FIGS. 3a–3f illustrate cross-sections of a known member 10 taken along the line 3—3 in FIG. 1 and show progressive degradation occurring most rapidly at the center shaded area 12 where the highest rate of degradation occurs in vivo. Degradation occurs when the polymer absorbs water and undergoes hydrolytic scission. Although degradation occurs throughout the member 10, the rate of degradation will generally be higher at a location having the lower pH as acidic environments catalyze degradation. The diffusion distance d of the solid member 10 is measured from the surface 14 to the center of the solid filament. As shown in FIGS. 3a–3f, the pH level is reduced in the center shaded area 12 of the solid member 10 because the acidic degradation by-products cannot rapidly migrate away from the location. The degradation rate nearer to the surface 14 of member 10 is relatively slower because the pH level at the surface 14 is not substantially changed since acid degradation by-products are more readily flushed or diffused away.

Figure 3A:
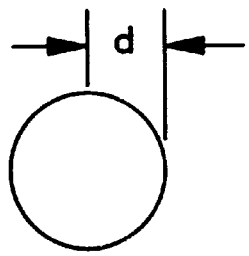
FIGS. 3a–3f are cross-sections of the example elongate member in FIG. 1 taken along the line 3—3 illustrating progressive degradation.
Figure 3B:
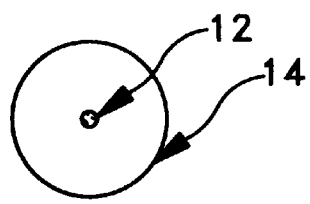
Figure 3C:
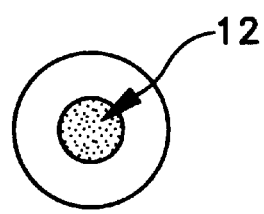
Figure 3D:
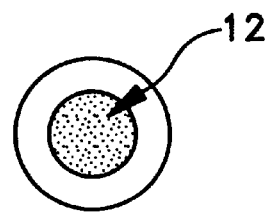
Figure 3E:
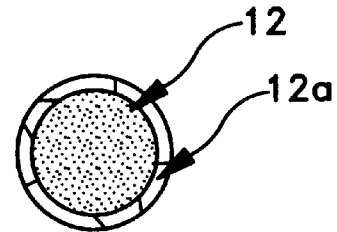
Figure 3F:
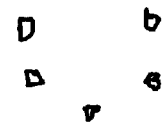

FIG. 3a represents the cross-section of a known substantially solid filament of an absorbable polymer, such as PLLA. In subsequent FIGS. 3b–3f, in vivo degradation is represented by shaded area 12; the darker shading in the Figures represents filament areas where the most degradation has occurred or where a faster rate of degradation is occurring. In FIG. 3b, the entire cross section is degrading, but the center shaded area 12 has degraded the most because acidic degradation products have accumulated there. The area of fast degradation progressively grows with time from the center toward the surface of the cross-section as shown in the increasing size of shaded area 12 in FIGS. 3c–3e. Finally, all that is left of structurally intact material of the substantially solid filament is a surface shell as shown in FIG. 3e. Cracks develop in the shell which lead to disintegration into fragments as shown in FIG. 3f.

Figure 2A:
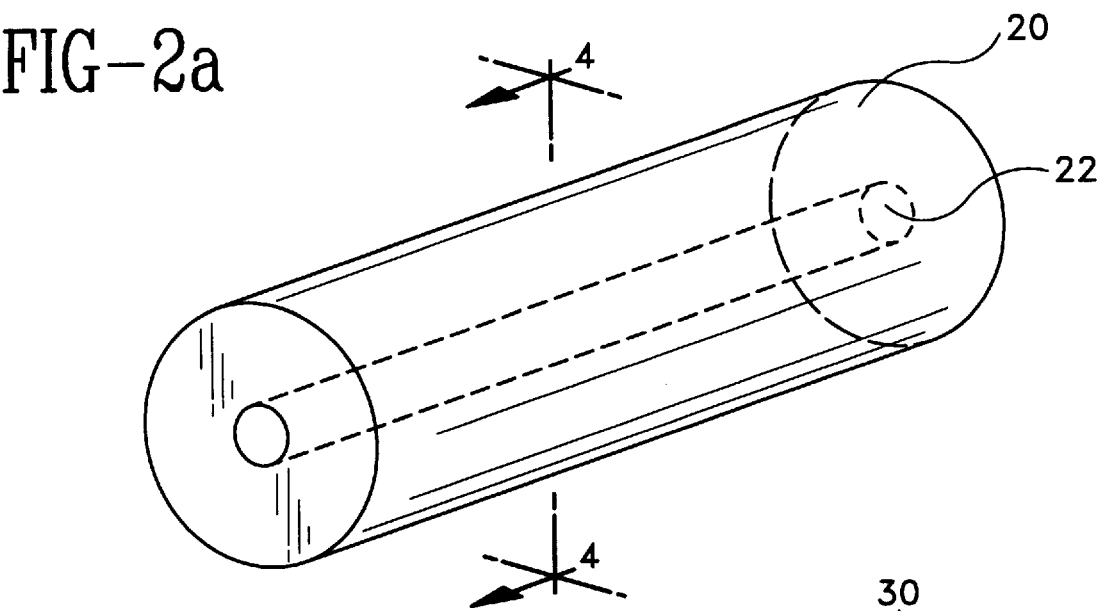
FIGS. 2a–2f are side views of six elongate elements of the present invention.
Figure 2B:
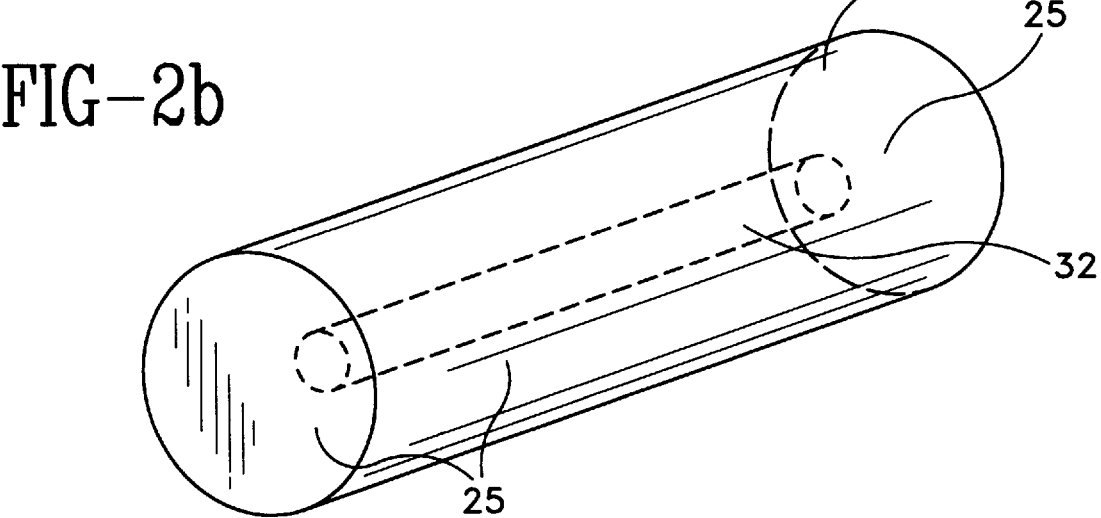
Figure 2C:
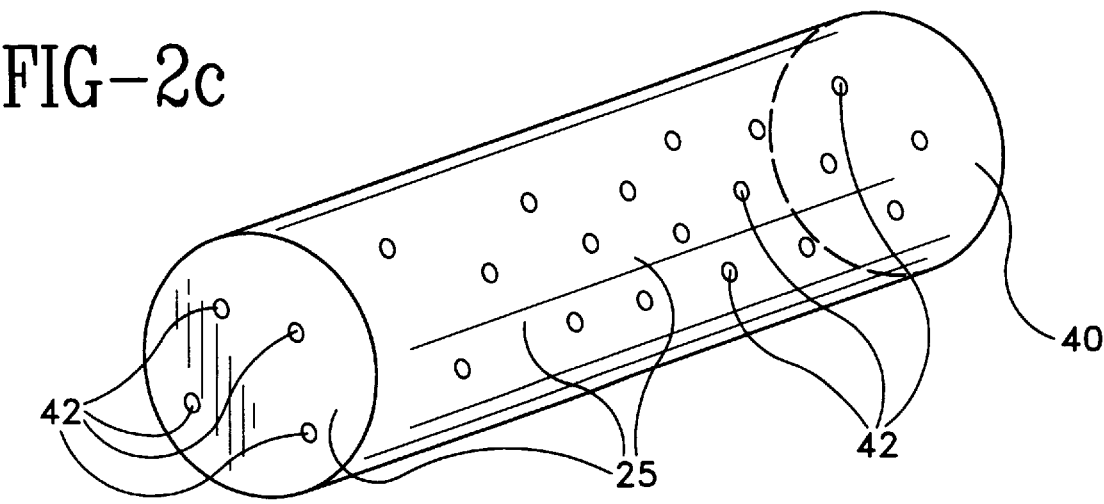
Figure 2D:
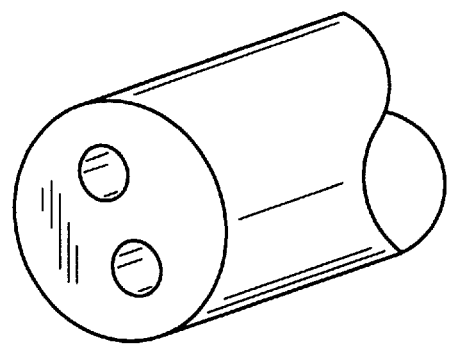
Figure 2E:
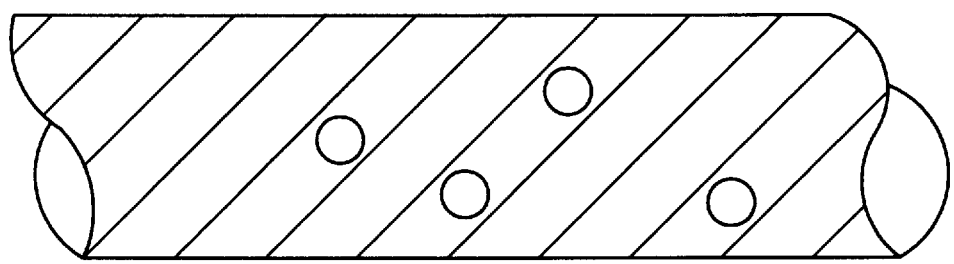
Figure 2F:
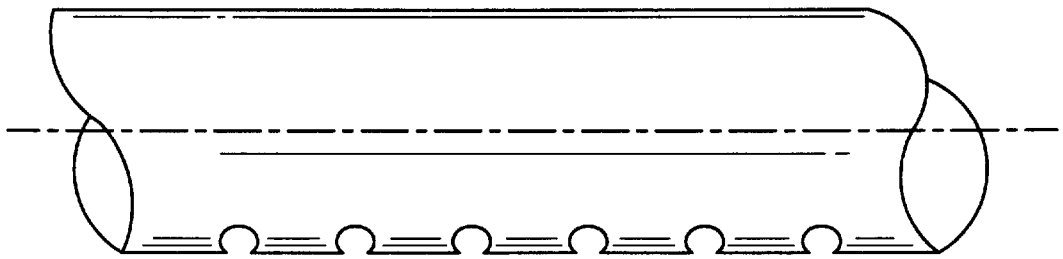

In comparison, reference is made to FIGS. 2a–2f showing filaments which advantageously provide accelerated degradation features compared to known materials. The filaments or elongate members have reservoir portions, specifically: elongate member 20 having at least one hollow 22 portion; elongate member 30 having at least one cavity 32 portion; and elongate member 40 having at least one porous 42 portion. The term "reservoir" is referred to as a volume of space internal to the filament where polymer degradation by-products are collected or stored. The reservoir may be both internal and external passages, with the external passages opening through a filament outside wall or end. FIG. 2a illustrates a hollow member with a center core; FIG. 2b illustrates a member having at least one cavity with sealed ends disposed inside the member; FIG. 2c illustrates a member having at least one pore (internal or external porosity, or both); FIG. 2d illustrates a multi-lumen member with a plurality of hollow portions; FIG. 2e illustrates a cross-section of a member having a plurality of internal pores; FIG. 2f illustrates a member having a plurality of surface pores. The external pores may connect with internal pores, cavites or hollow portions. The reservoir portions have a size greater than about 1 micron and having a volume percentage greater than about 10%. Elongate members may have one or more reservoir portions including combinations of hollow 22, cavity 32, or porous 42 portions.

Figure 4A:
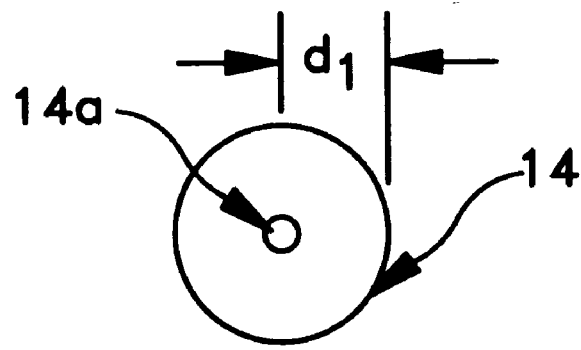
FIGS. 4a–4d are cross-sections of the elongate member in FIG. 2a taken along the line 4—4 illustrating progressive degradation.
Figure 4B:
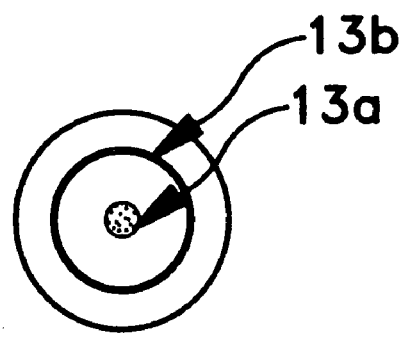
Figure 4C:
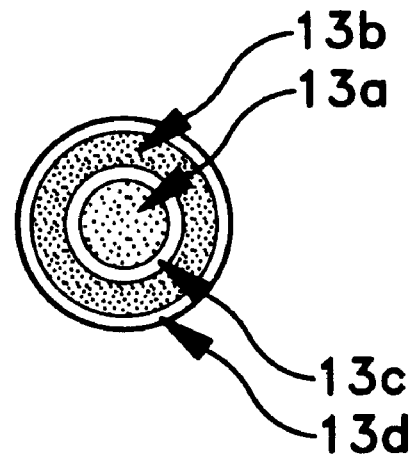
Figure 4D:
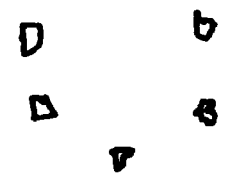

Reference is made to FIG. 4a which represents a member 20 from FIG. 2a having a manufactured hollow axial portion. When degradation begins as shown by the shading in FIG. 4b, the entire solid tubular section begins to deteriorate. In member 20, the shaded annular ring area 13b, shows that the center of the material mass degrades faster because of an accumulation of acidic degradation products in that annular shaded area. In addition, degradation products also accumulate in the hollow axial portion and deterioration of the hollow inner surface area 13a in member 20 is also accelerated. The member 20 generally degrades into a thin outer shell 13d and an internal ring 13c as shown in FIG. 4c. Cracks develop in the inner and outer ring which lead to disintegration as shown in FIG. 4d. Degradation and disintegration of member 20 is advantageously faster than the substantially solid member 10 because there are two regions of accelerated degradation, in areas 13a and 13b.

FIGS. 4a–4d illustrate cross-sections taken along the line 4—4 of FIG. 2a and show progressive degradation of the elongate member 20 in areas where the highest rate of degradation occurs in vivo. Although degradation occurs throughout the member 20, the rate of degradation is generally higher at a location having the lower pH as acidic environments catalyze degradation. By-products from degradation such as lactic acid or glycolic acid are stored in the hollow 22, cavity 32, or porous 42 portions which act as reservoirs and advantageously accelerate the degradation of the inner surfaces. The diffusion distance $d_1$ in elongate members 20, 30, 40 is relatively shorter than the diffusion distance d in elongate member 10. The diffusion distance $d_1$ is measured from the outside surface 14 to the inside surface 14a. In the present invention, the combination of generally shorter water absorption distance $d_1$, resulting generally shorter water absorption time, and relatively accelerated degradation at the by-product reservoir areas results in relatively faster overall polymer resorption of the elongate members 20, 30, and 40 or endoprosthesis 50 in vivo. The elongate members 20, 30, and 40 may further comprise one or more internal or external walls 25 that are adapted to bioabsorb in vivo. Tables 1 and 2 below describes preferred reservoir and endoprostheses embodiments.

TABLE 1

| Type of Reservoir: | % Volume Solid | % Volume Hollow or Cavity | Hollow or Cavity Features Dimensions |
|---|---|---|---|
| axial core (one lumen tubing) | 65–90 | 10–35 | Ø<50% of O.D. x length of filament strand |
| multi-lumen filament (two or more lumens) | 50–90 | 10–40 | Ø<50% of O.D./# of lumens, length of filament strand |
| internal porosity | 70–90 | 10–30 | 1–20 microns |
| external porosity (surface oriented) | 80–90 | 10–20 | 1–20 microns |

Figure 5:
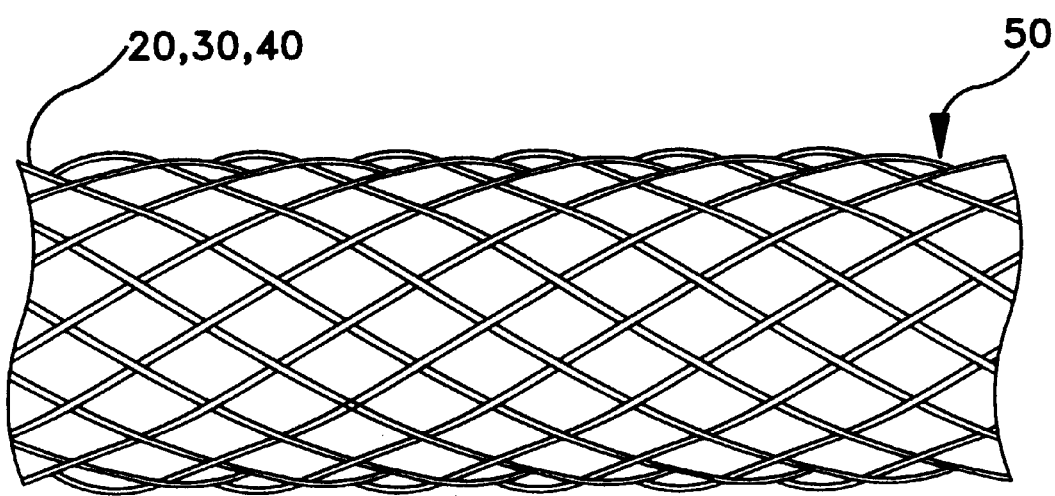
FIG. 5 is a side view of one embodiment of a braided endoprosthesis of the present invention.

Reference is made to FIG. 5 illustrating one embodiment of an implantable endoprosthesis 50 comprising elongate members made of a bioabsorbable polymer and having one or more hollow 22, cavity 32, or porous 42 portions (hollow, cavity, or porous portions not shown). The hollow 22, cavity 32, or porous 42 portions shorten the diffusion distance for water absorption and act as reservoirs to accumulate by-product from the degradation of the bioabsorbable material and thereby relatively increase the degradation rate of the structure. The bioabsorbable implantable endoprosthesis 50 may be elastically or plastically expandable and be made from polyester bioabsorbable polymers including PLA and PGA, as well as other polymers.

A bioabsorbable implantable prosthesis or stent 50 in accordance with the present invention is illustrated generally in FIG. 5. Stent 50 is a tubular device formed from elongated strands or filaments 20, 30, 40. The filaments 20, 30, 40 are interwoven to form an open mesh or weave construction. As described in greater detail below, at least one and preferably all filaments 20, 30, 40 consists of one or more commercially available grades of poly(alpha-hydroxy acid) such as poly-L-lactide (PLLA), poly-D-lactide (PDLA), polyglycolide (PGA), polydioxanone, polycaprolactone, polygluconate, polylactic acid-polyethylene oxide copolymers, poly (hydroxybutyrate), polyanhydride, polyphosphoester, poly (amino acids), or related copolymers materials. Methods for fabricating stents 50 are generally known and disclosed, for example, in the Wallsten U.S. Pat. No. 4,655,771 and the Wallsten et al. U.S. Pat. No. 5,061,275.

TABLE 2

| # Of Filament Strands In Braid | Braid Mandrel Diameter, mm | Braid Angle, Degrees | PLLA Diameter, mm | PDLA Diameter, mm | PLLA/PDLA Diameter, mm | PGA Diameter, mm |
|---|---|---|---|---|---|---|
| 10 | 3–6 | 120–150 | .15–.25 | .15–.25 | .15–.25 | .20–.30 |
| 10 | 3–6 | 120–150 | .20–.30 | .20–.30 | .20–.30 | .25–.35 |
| 12 | 3–8 | 120–150 | .20–.30 | .20–.30 | .20–.30 | .25–.35 |
| 12 | 3–8 | 120–150 | .35–.45 | .35–.45 | .35–.45 | .40–.50 |
| 15 | 6–10 | 120–150 | .30–.40 | .30–.40 | .30–.40 | .35–.45 |
| 15 | 6–10 | 120–150 | .35–.45 | .35–.45 | .35–.45 | .40–.50 |
| 18 | 7–12 | 120–150 | .35–.45 | .35–.45 | .35–.45 | .40–.50 |
| 18 | 7–12 | 120–150 | .40–.50 | .40–.50 | .40–.50 | .45–.55 |
| 20 | 3–9 | 120–150 | .20–.30 | .20–.30 | .20–.30 | .25–.35 |
| 24 | 8–12 | 120–150 | .20–.30 | .20–.30 | .20–.30 | .25–.35 |
| 24 | 9–14 | 120–150 | .25–.35 | .25–.35 | .25–.35 | .30–.40 |
| 24 | 12–18 | 120–150 | .30–.40 | .30–.40 | .30–.40 | .35–.45 |
| 30 | 16–26 | 120–150 | .30–.40 | .30–.40 | .30–.40 | .35–.45 |
| 36 | 20–30 | 120–150 | .35–.45 | .35–.45 | .35–.45 | .40–.50 |
| 24 | 14–20 | 120–150 | .35–.45 | .35–.45 | .35–.45 | .40–.50 |

| # Of Filament Strands In Braid | Braid Mandrel Diameter, Mm | Braid Angle, Degrees | PGA/PLLA Diameter, mm | PGA/ Polycaprolactone Diameter, mm | Polydioxanone Diameter, mm | PGA/trimethylene carbonate Diameter, mm |
|---|---|---|---|---|---|---|
| 10 | 3–6 | 120–150 | .20–.30 | .22–.32 | .25–.35 | .22–.32 |
| 10 | 3–6 | 120–150 | .25–.35 | .27–.37 | .30–.40 | .27–.37 |
| 12 | 3–8 | 120–150 | .25–.35 | .27–.37 | .30–.40 | .27–.37 |
| 12 | 3–8 | 120–150 | .40–.50 | .42–.52 | .45–.55 | .42–.52 |
| 15 | 6–10 | 120–150 | .35–.45 | .37–.47 | .40–.50 | .37–.47 |
| 15 | 6–10 | 120–150 | .40–.50 | .42–.52 | .45–.55 | .42–.52 |
| 18 | 7–12 | 120–150 | .40–.50 | .42–.52 | .45–.55 | .42–.52 |
| 18 | 7–12 | 120–150 | .45–.55 | .47–.57 | .50–.60 | .47–.57 |
| 20 | 3–9 | 120–150 | .25–.35 | .27–.37 | .30–.40 | .27–.37 |
| 24 | 8–12 | 120–150 | .25–.35 | .27–.37 | .30–.40 | .27–.37 |
| 24 | 9–14 | 120–150 | .30–.40 | .32–.42 | .35–.45 | .32–.42 |
| 24 | 12–18 | 120–150 | .35–.45 | .37–.47 | .40–.50 | .37–.47 |
| 30 | 16–26 | 120–150 | .35–.45 | .37–.47 | .40–.50 | .37–.47 |
| 36 | 20–30 | 120–150 | .40–.50 | .42–.52 | .45–.55 | .42–.52 |
| 24 | 14–20 | 120–150 | .40–.50 | .42–.52 | .45–.55 | .42–.52 |

Stent 50 is shown in its expanded or relaxed state FIG. 5 in the configuration it assumes when subject to no external loads or stresses. The filaments 20, 30, 40 are resilient, permitting the radial compression of stent 50 into a reduced-radius, extended-length configuration or state suitable for delivery to the desired placement or treatment site through a body vessel (i.e., transluminally). Stent 50 is also self-expandable from the compressed state, and axially flexible.

The tubular and self-expandable body or structure formed by the interwoven filaments 20, 30, 40 is a primary prosthetically-functional structure of stent 10, and for this reason the device can be considered to substantially consist of this structure to the exclusion of other structures. However, it is known that other structures and features can be included in stents, and in particular features which enhance or cooperate with the tubular and self-expandable structure or which facilitate the implantation of the structure. One example is the inclusion of radiopaque markers on the structure which are used to visualize the position of the stent through fluoroscopy during implantation. Another example is the inclusion of a covering or additional interwoven filaments, for instance, to reduce the porosity or open spaces in the structure so that the stent can be used to prevent tissue ingrowth or be used as a graft. Other examples include collapsing threads or other structures to facilitate repositioning and removal of the stent. Stents of these types nonetheless still substantially consist of the tubular and self-expandable structure formed by interwoven filaments 20, 30, 40.

In the present invention, the in-vivo absorption time of bioabsorbable implantable endoprosthesis 50 is dependent upon the absorbable polymer used in the device, material processing, and the implant environment (pH, chemical composition of fluids, mechanical loading). Each polymer has its own characteristic degradation rate in the body based on its composition and structure. The degradation rate is also affected by manufacturing, sterilization, storage, geometry, and the specific environment in which the polymer is implanted. For a given set of implant conditions, a specific absorption time may be designed by utilizing fast-absorbing or slow-absorbing polymer.

Each polymer also has different physical and mechanical properties. For example, PLA has a moderately high modulus and strength and high ductility and PGA has a high modulus and a lower ductility (stiff and relatively brittle). An endoprosthesis 50 may have bioabsorbable polymer elongate elements having a tensile modulus of from about 400,000 to about 2,000,000 psi. The preferred range of tensile modulus for an endoprosthesis 50 made of bioabsorbable polymer elongate elements is from about 700,000 to about 1,200,000 psi. A preferred embodiment of the bioabsorbable polymer elongate elements includes about a 1,000,000 psi tensile modulus and about a 90 ksi tensile strength. For structural elongate members 20, 30, 40 that are loaded primarily in bending or torsion, the maximum von Mises equivalent stresses are at the surface and the stress at the center of the elongate member is zero, so a hollow 22 portion may be used. It may be desirable to have the ductile properties of PLA and the short resorption time of PGA in one implant. One way to achieve this is to use copolymers of PLA and PGA, but this may result in a compromise of characteristics. The present invention allows the device designer to select the polymer based on desirable biocompatibility, and mechanical and physical properties with less concern for the material degradation rate by utilizing the one or more reservoir portion features to tailor the degradation rate beyond the rate that would be expected with a substantially solid material construction.

Bioabsorbable polymer surgical implants and sutures lose their original tensile strength and mass over a period of time in the environment of the body. The retention time of the original tensile strength is important, because the device or suture must serve its intended structural purpose for a period of time that is long enough to allow healing to occur. Subsequent to healing, the polymer may lose strength since the structural support is now performed by native tissue or bone. The healing time varies depending on the type of tissues involved; skin, tendon, bone, or muscle. A polymer with an appropriate strength retention time must be selected for each type of medical indication.

The polymer degradation rate is influenced by several intrinsic and extrinsic factors. Intrinsic factors include the chemical composition and physical structure of the polymer (such as substituents, orientation, level of crystallinity, geometry, and molecular weight). Extrinsic factors include the pH of the biological medium, electrolytes, external stress, temperature, radiation, free radicals, and enzymes.

The degradation of absorbable polymers is primarily due to hydrolysis. The hydrolytic reaction causes the polymer molecular chains to be broken and the chain length decreases with the duration of degradation. The result of decreasing chain length is a reduction in physical and mechanical properties. Loss of mass occurs when a significant number of chains are broken to allow diffusion of small molecular chains out of the polymer and into the biological environment. Disintegration of the device occurs when there has been loss of strength and mass and portions of the polymer fragment.

The three types of degradation properties that are used to describe the absorbable polymer degradation process are loss of tensile strength profile, loss of mass profile, and type of degradation products released into the surrounding tissues. The loss of tensile strength always precedes the other two events, because the absorbable polymers degrade by hydrolysis throughout the bulk of the material rather than from surface erosion. Bulk degradation causes the polymer to lose strength first and then to lose mass. If degradation were to occur by surface erosion, the polymer would lose mass before or at the same time as it loses strength.

All synthetic absorbable sutures are water-insoluble polymers. This means that the rate of diffusion of water is an important factor in determining the rate of hydrolysis and degradation. Thinner sections should theoretically reach the bulk water concentration level where hydrolysis can start to occur faster than thick sections. However, once degradation starts, thicker sections will have faster degradation rates because the acidic degradation products in the center of the section build up and catalyze degradation to a faster rate than in other locations in the material where diffusion distances are shorter and the degradation products migrate to the surface and are buffered by the biological environment. The result is that the degradation profile is at a maximum at the center of the solid section and decreases from the center to the surface. Degradation occurs throughout the bulk, but is faster in the center. In, for example, a hollow section where degradation products can collect in the reservoir, there are two locations of high degradation rate; the surface of the member at the reservoir and the center of the solid section. Therefore, the degradation of a hollow piece should occur sooner than a solid piece because the diffusion distance for water absorption is shorter and because there are two fast-degrading fronts in the material.

For PLA, structural degradation occurs over a time interval of about 6 months to 2 years in-vivo. A member will disintegrate after it loses enough strength and is no longer capable of withstanding applied loads or is no longer capable of holding itself together. Structural degradation takes place long after the time needed for endothelialization or epithelialization of the device.

Absorption occurs when polymer degradation products are released from the device and introduced into normal body chemical processes. Metabolism is the chemical changes in living cells by which energy is provided for vital processes and activities and new material is assimilated to repair the waste.

Excretion is separation and elimination or discharge from the blood or tissues of useless, superfluous, or harmful material that is eliminated from the body. Excretion differs from a secretion in not being produced to perform a useful function.

The biocompatibility of absorbable polymers during degradation depends upon the rate of accumulation and how well the surrounding tissue or fluid buffers or metabolizes the degradation products. If the products are metabolizable, the rate at which this will occur is dependent upon the blood circulation in the tissue. A well-vascularized lumen wall could buffer and metabolize degradation products as they are released from the implant. This biological process is important to minimize adverse tissue reaction to the degrading implant.

The final degradation products from PLLA and PGA are lactic and glycolic acid which are normally present in the human body. The acids are metabolized by cells around the implant. The metabolization process is a citrate cycle which converts the acids to carbon dioxide which is respirated out of the body.

For a PLA member, mass degradation is completed with total absorption of the polymer endoprosthesis in about 1.5 to 3 years after implantation.

To manufacture the implantable endoprosthesis 50, the tubular braided filament endoprosthesis 50 is disposed on a stainless steel tubular mandrel (not shown) and held in an axially compressed position, axially extended position, or a free state position with plastic tie-wraps or comparable instruments (not shown) to form an assembly. The term "free state" is used when no externally applied forces are acting on the device, for example, when the device is resting on a table. The assembly is annealed at a temperature less than the melting point of the endoprosthesis 50 for a time of from about 5 minutes to about 90 minutes. The endoprosthesis 50 may be annealed at a temperature of from about 130° C. to about 160° C. for about 10 minutes to about 20 minutes. A preferable annealing process includes temperature at about 140° C. for about 15 minutes in air, vacuum, argon, helium, or combinations thereof. Thereafter, the assembly is cooled to a room temperature, and the endoprosthesis 50 is slid off of the mandrel. The implantable endoprosthesis 50 is then cut to predetermined longitudinal lengths by clipping the entire endoprosthesis 50 or each filament crossing point.

The hollow 22, cavity 32, or porous 42 portions may be made by an extrusion process using mandrels or by coring during injection molding. Porosity may be made by processes including machining, dissolvable microspheres, extrusion or molding parameter selection, gas bubbling, or like methods.

Examples of the present invention are described below.

EXAMPLE 1

In an experiment, a solid extruded PLLA rod (solid rod) and an extruded PLLA rod having two cavity portions (cavity rod) were used to demonstrate faster absorption of the cavity rod. The solid rod and the cavity rod were made from the same initial solid rod which was first annealed in air at 140° C. for about 15 minutes. The solid rod was cut into 0.6"–0.7" (15.2 mm–17.8 mm) lengths.

The solid rod had a measured outside diameter of about 0.212" (5.4 mm) and had a length of about 0.6"–0.7" (15.2 mm–17.8 mm). The cavity rod measured an outside diameter of about 0.212" (5.4 mm), and had a length of about 0.6"–0.7" (15.2 mm–17.8 mm), and included cavities at each end measuring 5/64" (2 mm) diameter by 0.2"–0.3" (5 mm–7 mm) deep. The cavity rod was made by using one of the solid PLLA lengths and drilling an axial hole at each end using a 5/64" (2 mm) drill a depth of 0.2"–0.3" (5 mm–7 mm). The cavity opening at the end of each axial hole was covered with medical grade Dow silicone adhesive A, thus creating two internal cavities in the rod to form the cavity rod.

The solid rod and the cavity rod were put in separate 32 oz. jars filled with a phosphate buffered saline (PBS) solution (pH=7.4). Each jar was incubated at 60° C. The solid rod and the cavity rod were each inspected for weight change and for evidence of fracture on a regular basis. The weight of the solid rod and the cavity rod included the by products of degradation.

The solid rod and the cavity rod were weighed prior to the experiment (day 0) and on the following days of the experiment: 3, 4, 5, 6, 7, 10, 11, 12, 13, 14, 17, 18, 19, 20, 21, 22, 25, and 26. The solid rod and the cavity rod were not weighed on the following days of the experiment: 1, 2, 8, 9, 15, and 16.

The results of the experiment showed that both the solid rod and the cavity rod gained weight for the first 10 days (presumably from water absorption); and that the cavity rod gained weight faster than the solid rod. The solid rod and the cavity rod began losing weight after 10 days of incubation (presumably from polymer degradation). The cavity rod fractured at 22 days of incubation with about 0.6% loss of its original specimen weight as compared to the solid rod which fractured at 26 days of incubation with about 1.3% loss of its original specimen weight. Testing and measurements were completed when fracture of each respective rod occurred.

Bioabsorbable member or device fracture (disintegration) is an important milestone in the process of bioabsorption because it marks the certain end to the functional usefulness of the member or device in the body. At the point of disintegration, the member or device can no longer provide luminal support and degrades away in the body. Disintegration is a useful measure of degradation time because it is easy to measure through observation and compared.

Table 3 shows measurements recorded during the experiment in tabular form. FIG. 6 illustrates the results of the experiment from Table 3 in graphical form.

TABLE 3

| days | Cavity rod, g | Solid rod, g | % loss of mass, (cavity) | % loss of mass, (solid) |
|---|---|---|---|---|
| 0 | 0.4211 | 0.5005 | 0 | 0 |
| 1 | no measurement | no measurement | | |
| 2 | no measurement | no measurement | | |
| 3 | 0.4211 | 0.5005 | 0 | 0 |
| 4 | 0.4227 | 0.5023 | −0.4 | −0.4 |
| 5 | 0.4245 | 0.5044 | −0.8 | −0.8 |
| 6 | 0.4268 | 0.5061 | −1.4 | −1.1 |

TABLE 3-continued

| days | Cavity rod, g | Solid rod, g | % loss of mass, (cavity) | % loss of mass, (solid) |
|---|---|---|---|---|
| 7 | 0.4295 | 0.5081 | −2 | −1.5 |
| 8 | no measurement | no measurement | | |
| 9 | no measurement | no measurement | | |
| 10 | 0.4408 | 0.5178 | −4.7 | −3.5 |
| 11 | 0.4351 | 0.5145 | −3.3 | −2.8 |
| 12 | 0.4326 | 0.5123 | −2.7 | −2.4 |
| 13 | 0.432 | 0.5108 | −2.6 | −2.1 |
| 14 | 0.4296 | 0.5082 | −2 | −1.5 |
| 15 | no measurement | no measurement | | |
| 16 | no measurement | no measurement | | |
| 17 | 0.4262 | 0.5041 | −1.2 | −0.7 |
| 18 | 0.4244 | 0.503 | −0.8 | −0.5 |
| 19 | 0.4248 | 0.5027 | −0.9 | −0.4 |
| 20 | 0.424 | 0.5025 | −0.7 | −0.4 |
| 21 | 0.4236 | 0.5025 | −0.6 | −0.4 |
| 22 | 0.4184 | 0.4979 | 0.6 | 0.5 |
| 25 | | 0.4944 | | 1.2 |
| 26 | | 0.4938 | | 1.3 |

In sum, the cavity rod fractured in less time than the solid rod. The cavity rod fractured in 22 days as compared to the solid rod which fractured in 26 days. Also, the cavity rod required less mass degradation prior to fracture than the solid rod. The experiment demonstrated that a PLLA bioabsorbable member having two cavities would degrade faster than a solid member. The faster degradation was found to result from a shorter diffusion distance across the section thickness and from acceleration of degradation on the inner surface of the cavity from collection of acidic degradation products. The absorption time for the cavity rod could be made to be longer or shorter by changing the volume percentage of the cavity areas or changing the geometry of the reservoir area (i.e. round, elongate, small or large). Furthermore, the degradation rate of bioabsorbable implantable endoprostheses may be manipulated without changing materials or processing methods.

EXAMPLE 2

Stents 50 can be fabricated from 10 filament strands of 0.15–0.25 mm diameter PLLA, PDLA, PLLA-PDLA copolymer, 0.20–0.30 mm diameter PGA, PGA-PLLA copolymer, 0.22–0.32 mm diameter PGA-polycaprolactone copolymer, PGA-trimethylene carbonate copolymer, or 0.25–0.35 mm diameter polydioxanone. The filaments with reservoirs in the form of hollow cores with diameters less than about 50% of the filament outer diameter extending over the entire filament length (except for sealed ends at the end of each filament that may occur during manufacturing); cavities with diameters less than about 50% of the filament outer diameter extending over one or portions of the entire filament length; or pores with diameters of about one to about twenty microns. The filaments are disposed on a 3–6 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel, and cut to the desired stent length.

EXAMPLE 3

Stents 50 can be fabricated from 10 filament strands of 0.20–0.30 mm diameter PLLA, PDLA, PLLA-PDLA copolymer, 0.25–0.35 mm diameter PGA, PGA-PLLA copolymer, 0.27–0.37 mm diameter PGA-polycaprolactone copolymer, PGA-trimethylcarbonate copolymer, or 0.30–0.40 mm diameter polydioxanone. The filaments with reservoirs in the form of hollow cores with diameters less than about 50% of the filament outer diameter extending over the entire filament length (except for sealed ends at the end of each filament that may occur during manufacturing); cavities with diameters less than about 50% of the filament outer diameter extending over one or portions of the entire filament length; or pores with diameters of about one to about twenty microns. The filaments are disposed on a 3–6 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel, and cut to the desired stent length.

EXAMPLE 4

Stents 50 can be fabricated from 12 filament strands of 0.20–0.30 mm diameter PLLA, PDLA, PLLA-PDLA copolymer, 0.25–0.35 mm diameter PGA, PGA-PLLA copolymer, 0.27–0.37 mm diameter PGA-polycaprolactone copolymer, PGA-trimethylcarbonate copolymer, or 0.30–0.40 mm diameter polydioxanone. The filaments with reservoirs in the form of hollow cores with diameters less than about 50% of the filament outer diameter extending over the entire filament length (except for sealed ends at the end of each filament that may occur during manufacturing); cavities with diameters less than about 50% of the filament outer diameter extending over one or portions of the entire filament length; or pores with diameters of about one to twenty microns. The filaments are disposed on a 3–8 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel and cut to the desired stent length.

EXAMPLE 5

Stents 50 can be fabricated from 12 filament strands of 0.35–0.45 mm diameter PLLA, PDLA, PLLA-PDLA copolymer, 0.40–0.50 mm diameter PGA, PGA-PLLA copolymer, 0.42–0.52 mm diameter PGA-polycaprolactone copolymer, PGA-trimethylcarbonate copolymer, or 0.45–0.55 mm diameter polydioxanone. The filaments with reservoirs in the form of hollow cores with diameters less than about 50% of the filament outer diameter extending over the entire filament length (except for sealed ends at the end of each filament that may occur during manufacturing); cavities with diameters less than about 50% of the filament outer diameter extending over one or portions of the entire filament length; or pores with diameters of about one to twenty microns. The filaments are disposed on a 3–8 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel and cut to the desired stent length.

EXAMPLE 6

Stents 50 can be fabricated from 15 filament strands of 0.30–0.40 mm diameter PLLA, PDLA, PLLA-PDLA copolymer, 0.35–0.45 mm diameter PGA, PGA-PLLA copolymer, 0.37–0.47 mm diameter PGA-polycaprolactone copolymer, PGA-trimethylcarbonate copolymer, or 0.40–0.50 mm diameter polydioxanone. The filaments with reservoirs in the form of hollow cores with diameters less than about 50% of the filament outer diameter extending over the entire filament length (except for sealed ends at the end of each filament that may occur during manufacturing); cavities with diameters less than about 50% of the filament outer diameter extending over one or portions of the entire filament length; or pores with diameters of about one to twenty microns. The filaments are disposed on a 6–10 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel and cut to the desired stent length.

EXAMPLE 7

Stents 50 can be fabricated from 15 filament strands of 0.35–0.45 mm diameter PLLA, PDLA, PLLA-PDLA copolymer, 0.40–0.50 mm diameter PGA, PGA-PLLA copolymer, 0.42–0.52 mm diameter PGA-polycaprolactone copolymer, PGA-trimethylcarbonate copolymer, or 0.45–0.55 mm diameter polydioxanone. The filaments with reservoirs in the form of hollow cores with diameters less than about 50% of the filament outer diameter extending over the entire filament length (except for sealed ends at the end of each filament that may occur during manufacturing); cavities with diameters less than about 50% of the filament outer diameter extending over one or portions of the entire filament length; or pores with diameters of about one to twenty microns. The filaments are disposed on a 6–10 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel and cut to the desired stent length.

EXAMPLE 8

Stents 50 can be fabricated from 18 filament strands of 0.35–0.45 mm diameter PLLA, PDLA, PLLA-PDLA copolymer, 0.40–0.50 mm diameter PGA, PGA-PLLA copolymer, 0.42–0.52 mm diameter PGA-polycaprolactone copolymer, PGA-trimethylcarbonate copolymer, or 0.45–0.55 mm diameter polydioxanone. The filaments with reservoirs in the form of hollow cores with diameters less than about 50% of the filament outer diameter extending over the entire filament length (except for sealed ends at the end of each filament that may occur during manufacturing); cavities with diameters less than about 50% of the filament outer diameter extending over one or portions of the entire filament length; or pores with diameters of about one to twenty microns. The filaments are disposed on a 7–12 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel and cut to the desired stent length.

EXAMPLE 9

Stents 50 can be fabricated from 18 filament strands of 0.40–0.50 mm diameter PLLA, PDLA, PLLA-PDLA copolymer, 0.45–0.55 mm diameter PGA, PGA-PLLA copolymer, 0.47–0.57 mm diameter PGA-polycaprolactone copolymer, PGA-trimethylcarbonate copolymer, or 0.50–0.60 mm diameter polydioxanone. The filaments with reservoirs in the form of hollow cores with diameters less than about 50% of the filament outer diameter extending over the entire filament length (except for sealed ends at the end of each filament that may occur during manufacturing); cavities with diameters less than about 50% of the filament outer diameter extending over one or portions of the entire filament length; or pores with diameters of about one to twenty microns. The filaments are disposed on a 7–12 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel and cut to the desired stent length.

EXAMPLE 10

Stents 50 can be fabricated from 20 filament strands of 0.20–0.30 mm diameter PLLA, PDLA, PLLA-PDLA copolymer, 0.25–0.35 mm diameter PGA, PGA-PLLA copolymer, 0.27–0.37 mm diameter PGA-polycaprolactone copolymer, PGA-trimethylcarbonate copolymer, or 0.30–0.40 mm diameter polydioxanone. The filaments with reservoirs in the form of hollow cores with diameters less than about 50% of the filament outer diameter extending over the entire filament length (except for sealed ends at the end of each filament that may occur during manufacturing); cavities with diameters less than about 50% of the filament outer diameter extending over one or portions of the entire filament length; or pores with diameters of about one to twenty microns. The filaments are disposed on a 3–9 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel and cut to the desired stent length.

EXAMPLE 11

Stents 50 can be fabricated from 24 filament strands of 0.20–0.30 mm diameter PLLA, PDLA, PLLA-PDLA copolymer, 0.25–0.35 mm diameter PGA, PGA-PLLA copolymer, 0.27–0.37 mm diameter PGA-polycaprolactone copolymer, PGA-trimethylcarbonate copolymer, or 0.30–0.40 mm diameter polydioxanone. The filaments with reservoirs in the form of hollow cores with diameters less than about 50% of the filament outer diameter extending over the entire filament length (except for sealed ends at the end of each filament that may occur during manufacturing); cavities with diameters less than about 50% of the filament outer diameter extending over one or portions of the entire filament length; or pores with diameters of about one to twenty microns. The filaments are disposed on a 8–12 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel and cut to the desired stent length.

EXAMPLE 12

Stents 50 can be fabricated from 24 filament strands of 0.25–0.35 mm diameter PLLA, PDLA, PLLA-PDLA copolymer, 0.30–0.40 mm diameter PGA, PGA-PLLA copolymer, 0.32–0.42 mm diameter PGA-polycaprolactone copolymer, PGA-trimethylcarbonate copolymer, or 0.35–0.45 mm diameter polydioxanone. The filaments with reservoirs in the form of hollow cores with diameters less than about 50% of the filament outer diameter extending over the entire filament length (except for sealed ends at the end of each filament that may occur during manufacturing); cavities with diameters less than about 50% of the filament outer diameter extending over one or portions of the entire filament length; or pores with diameters of about one to twenty microns. The filaments are disposed on a 9–14 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel and cut to the desired stent length.

EXAMPLE 13

Stents 50 can be fabricated from 24 filament strands of 0.30–0.40 mm diameter PLLA, PDLA, PLLA-PDLA copolymer, 0.35–0.45 mm diameter PGA, PGA-PLLA copolymer, 0.37–0.47 mm diameter PGA-polycaprolactone copolymer, PGA-trimethylcarbonate copolymer, or 0.40–0.50 mm diameter polydioxanone. The filaments with reservoirs in the form of hollow cores with diameters less than about 50% of the filament outer diameter extending over the entire filament length (except for sealed ends at the end of each filament that may occur during manufacturing); cavities with diameters less than about 50% of the filament outer diameter extending over one or portions of the entire filament length; or pores with diameters of about one to twenty microns. The filaments are disposed on a 12–18 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel and cut to the desired stent length.

EXAMPLE 14

Stents 50 can be fabricated from 30 filament strands of 0.30–0.40 mm diameter PLLA, PDLA, PLLA-PDLA copolymer, 0.35–0.45 mm diameter PGA, PGA-PLLA copolymer, 0.37–0.47 mm diameter PGA-polycaprolactone copolymer, PGA-trimethylcarbonate copolymer, or 0.40–0.50 mm diameter polydioxanone. The filaments with reservoirs in the form of hollow cores with diameters less than about 50% of the filament outer diameter extending over the entire filament length (except for sealed ends at the end of each filament that may occur during manufacturing); cavities with diameters less than about 50% of the filament outer diameter extending over one or portions of the entire filament length; or pores with diameters of about one to twenty microns. The filaments are disposed on a 16–26 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel and cut to the desired stent length.

EXAMPLE 15

Stents 50 can be fabricated from 36 filament strands of 0.35–0.45 mm diameter PLLA, PDLA, PLLA-PDLA copolymer, 0.40–0.50 mm diameter PGA, PGA-PLLA copolymer, 0.42–0.52 mm diameter PGA-polycaprolactone copolymer, PGA-trimethylcarbonate copolymer, or 0.45–0.55 mm diameter polydioxanone. The filaments with reservoirs in the form of hollow cores with diameters less than about 50% of the filament outer diameter extending over the entire filament length (except for sealed ends at the end of each filament that may occur during manufacturing); cavities with diameters less than about 50% of the filament outer diameter extending over one or portions of the entire filament length; or pores with diameters of about one to twenty microns. The filaments are disposed on a 20–30 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel and cut to the desired stent length.

EXAMPLE 16

Stents 50 can be fabricated from 24 filament strands of 0.35–0.45 mm diameter PLLA, PDLA, PLLA-PDLA copolymer, 0.40–0.50 mm diameter PGA, PGA-PLLA copolymer, 0.42–0.52 mm diameter PGA-polycaprolactone copolymer, PGA-trimethylcarbonate copolymer, or 0.45–0.55 mm diameter polydioxanone. The filaments with reservoirs in the form of hollow cores with diameters less than about 50% of the filament outer diameter extending over the entire filament length (except for sealed ends at the end of each filament that may occur during manufacturing); cavities with diameters less than about 50% of the filament outer diameter extending over one or portions of the entire filament length; or pores with diameters of about one to twenty microns. The filaments are disposed on a 14–20 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel and cut to the desired stent length.

It will be evident from considerations of the foregoing that the bioabsorbable implantable endoprosthesis may be constructed using a number of methods and materials, in a wide variety of sizes and styles for the greater efficiency and convenience of a user.

A bioabsorbable stent that may advantageously be used in conjunction with the present invention is disclosed in J. Stinson's entitled "Bioabsorbable Self-Expanding Stent", U.S. patent application Ser. No. 08/904,467, filed concurrently herewith, and commonly assigned to the assignee of this application.

A bioabsorbable marker that may advantageously be used in conjunction with the present invention is disclosed in J. Stinson's and Claude Clerc's entitled "Radiopaque Markers And Methods Of Using Same", U.S. patent application Ser. No. 08/905,821, filed concurrently herewith, and commonly assigned to the assignee of this application.

Another bioabsorbable marker that may advantageously be used in conjunction with the present invention is disclosed in J. Stinson's entitled "Bioabsorbable Marker Having Radiopaque Constituents And Method Of Using Same", U.S. patent application Ser. No. 08/904,951, filed concurrently herewith, and commonly assigned to the assignee of this application.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

I claim:

1. A bioabsorbable implantable endoprosthesis comprising:

a tubular, radially compressible, axially flexible, and radially self-expandable braided and annealed structure having a diameter in a free state, the structure including from about 10 to about 36 filaments including poly (alpha-hydroxy acid), the structure having a radial force of from about 40 grams to about 300 grams at about one-half diameter, each filament having a tensile strength of from about 20 ksi to about 120 ksi, and a tensile modulus of from about 400,000 psi to about 2,000,000 psi, and an average diameter of from about 0.15 mm to about 0.6 mm, the filaments having a crossing angle of from about 120 degrees to about 150 degrees in a free state, each filament including one or more reservoir portions with an average cross-sectional area greater than about $7.9 \times 10^{-7}$ mm$^2$ and in each filament, the sum of the one or more reservoir portions when empty represents a total volume percentage greater than about 10% of the total filament volume.

2. The bioabsorbable implantable endoprosthesis of claim 1 wherein the sum of the one or more reservoir portions when empty represents a total volume percentage of from about 20% to about 40%.

3. The bioabsorbable implantable endoprosthesis of claim 1 wherein the degradation by-products at least partially collect in the reservoir portions.

4. The bioabsorbable implantable endoprosthesis of claim 1 wherein the degradation by-products in the reservoir portions have an average pH level which decreases over time in vivo.

5. The bioabsorbable implantable endoprosthesis of claim 1 wherein the reservoir portions are hollow, cavity, porous, or combinations thereof.

6. The bioabsorbable implantable endoprosthesis of claim 3 wherein the average pH level in the reservoir is between about 3 and 7.

7. The bioabsorbable implantable endoprosthesis of claim 1 wherein the endoprosthesis substantially degrades in vivo in less than 3 years.

8. The bioabsorbable implantable endoprosthesis of claim 1 wherein the endoprosthesis provides structural integrity to a body lumen for less than 2 years.

9. The bioabsorbable implantable endoprosthesis of claim 1 wherein the filaments are mono-filament, multi-filament, ribbon, suture, thread, fiber, or combinations thereof.

10. The bioabsorbable implantable endoprosthesis of claim 1 wherein the implantable endoprosthesis is a stent, stent-graft, graft, filter, occlusive device, or valve.

11. The bioabsorbable implantable endoprosthesis of claim 1 wherein the filaments gain weight in vivo in an amount of from about 0.1% to about 20% of initial mass prior to losing weight in an amount of from about 0.1% to about 70% of initial mass prior to disintegration.

12. The bioabsorbable implantable endoprosthesis of claim 1 wherein the reservoir portions accumulate the degradation by-product for a predetermined amount of time.

13. The bioabsorbable implantable endoprosthesis of claim 1 wherein the filaments comprise PLLA, PDLA, or combinations thereof and substantially degrade in vivo in from about 1 year to about 2 years.

14. The bioabsorbable implantable endoprosthesis of claim 1 wherein the filaments comprise polylactide, polyglycolide, or combinations thereof and substantially degrade in vivo in from about 3 months to about 1 year.

15. The bioabsorbable implantable endoprosthesis of claim 1 wherein the filaments comprise polyglycolide, polygluconate, polydioxanone, or combinations thereof and substantially degrade in vivo in from about 1 week to about 3 months.

16. The bioabsorbable endoprosthesis of claim 1 wherein the thickness of the filament t, in mm, is equal to about $(D/(1.8D+15)) \pm 0.03$ mm, where D, in mm, is the free state diameter.

17. The bioabsorbable endoprosthesis of claim 1 wherein the number of filaments, N, is equal to about (D/(0.022D+0.17))±4 filaments, where D, in mm, is the free state diameter.

18. The bioabsorbable endoprosthesis of claim 1 wherein the endoprosthesis has at least one end of diminishing diameter.

19. The bioabsorbable endoprosthesis of claim 1 wherein the filaments have a tensile modulus of from about 700,000 to about 1,200,000 psi.

20. The bioabsorbable endoprosthesis of claim 1 wherein the endoprosthesis has a braid angle of from about 60 degrees to about 150 degrees when implanted in vivo.

21. The bioabsorbable endoprosthesis of claim 1 wherein the filament further comprises a water absorption diffusion distance of from about 1 micron to about 250 microns.

22. The bioabsorbable implantable endoprosthesis of claim 21 further comprising hollow portions when empty which represent a volume percentage of at least 10 percent, cavity portions when empty which represent a volume percentage of at least 10 percent, and porous portions when empty which represent a volume percentage of at least 10 percent.

* * * * *